United States Patent [19]
Wurzel et al.

[11] Patent Number: 5,833,926
[45] Date of Patent: *Nov. 10, 1998

[54] ANALYTICAL AND DOSING SYSTEM

[75] Inventors: Christian Wurzel; Brigitte Wittmann-Liebold, both of Berlin, Germany

[73] Assignee: WITA GmbH, Germany

[*] Notice: This patent issued on a continued prosecution application filed under 37 CFR 1.53(d), and is subject to the twenty year patent term provisions of 35 U.S.C. 154(a)(2).

[21] Appl. No.: 547,454

[22] Filed: Oct. 24, 1995

[30] Foreign Application Priority Data

Oct. 24, 1994 [DE] Germany .................. 44 38 785.7

[51] Int. Cl.⁶ .................................................. G01N 33/48
[52] U.S. Cl. ............................... 422/81; 422/103; 436/86
[58] Field of Search .................... 436/86, 89; 422/61, 422/58, 100, 102–103, 82.03, 81, 82.05, 82.07, 70

[56] References Cited

U.S. PATENT DOCUMENTS 3,799,742  3/1974  Coleman .
5,391,353  2/1995  Graffunder ............................ 422/103

FOREIGN PATENT DOCUMENTS

93/22058  11/1993  WIPO .

OTHER PUBLICATIONS

Peter Jungblut, et al; "Protein Composition of the Human Heart: The Construction of a Myocardial Two–dimensioanl Electrophoresis Database"; *Electrophoresis* 1994, 15; pp. 685–707.

P. Edman, et al; "A Protein Sequenator"; *European J. Biochem*; vol. 1, No. 1, 1967; pp. 80–91.

B. Wittmann–Liebold, et al; "A Device Coupled to a Modified Sequentator for the Automated Conversion of Anilinothiazoliones into PTH Amino Acids"; *Analytical Biochemistry* 75 1976; pp. 621–633.

K. Ashman, et al; "A New Isocratic HPLC Separation for Pth–amino Acids, Based on 2–propanol"; Oct. 1985; *Elsevier Science Publishers B.V.*; vol. 190, No. 1; pp. 129–132.

*Primary Examiner*—Lyle A. Alexander
*Attorney, Agent, or Firm*—Londa and Traub LLP

[57] ABSTRACT

This invention describes a new analysis and dosing system and a method to manufacture such devices based on the latest microelectronic and micromachining working methods. On chip or wafer 1 which consists of the one- or multilayer substrate 2 and one- or multilayer cover 3, are arranged the essential construction components as reactor 6a, detector 6b, converter/collector 6c, injection valve 6d, micropumps, sensors, and valves V1 to V30, of the system, and the connection(s) to a detecting/metering device. The substrate 2 and/or the cover 3 show depressions 4 to build cavities and the co-operation of the elements 6a . . . 6n.

20 Claims, 4 Drawing Sheets

ANALYTICAL AND DOSING SYSTEM

This invention relates to a multi step reaction, analysis and dosing system and is applicable to sequential, stepwise and analysis and the exact and reproducible metering and dosing of the smallest quantities of substances in the range of <1µl. Preferred applications of the invention are the sequence analysis of proteins and peptides, and DNA-sequencing in biomedicine.

BACKGROUND

As described by Jungblut et al. in *Elektrophoresis* 15, 1994, pages 685 to 707, it is possible to diagnose diseases in their early stages of development, if one can successfully identify, on two-dimensional gels, those proteins which are changed because of the disease. This can be achieved if these protein variations manifest themselves in strong protein spots on the gels. The protein spots can be blotted on suitable chemically inert membranes and the blots can be sequenced in a sequencer. Alternatively, the proteins can be extracted from the gels for further analysis.

The protein and peptide sequencer is an automate for the determination of the amino acid sequence of a polypeptide chain by the stepwise Edman degradation (Edman, P. and Begg, G. 1967, Eur. J. Biochem. 1, 80–91) of the amino acids from the amino-terminal end. Under alkaline conditions, the N-terminal amino group is coupled with a coupling reagent, e.g. phenylisothiocyanante (PITC) under formation of the phenylthiocarbamoyl peptide derivative. After removal of the excess reagent, the base and other by-products, the first amino acid is cleaved off the polypeptide chain by treatment with anbydraus, strong acid (e.g. trifluoroacetic acid) and this first, N-terminal amino acid is released as a 2-anilino-thiazolinone amino acid derivative which is extracted from the rest of the polypeptide chain by organic solvents. It is transferred on-line into the converter (Wittmann-Liebold, B. Graffunder, H. Kohls, H. 1976 Anal. Biochem. 75, 621–633) where the isomerization takes place under formation of the more stable phenylhydantoin derivative of the amino acid (PTH-amino acid). The PTH-amino acids are identified by on-line HPLC separation and UV detection (Ashman, K. and Wittmann-Liebold, B. 1985, FEBS-Letters 190, 129–132). The following amino acid of the polypeptide chain, the second residue, is determined by subjecting the resulting polypeptide chain to a second round of Edman degradation and in further repeats of the degradation cycle the successive amino acid residues are determined.

By the degradation one obtains the amino-terminal (N-terminal) sequence of the first 10–100 amino acid residues. This sequence has to be compared with the already known sequences of proteins in protein databases and can therefore be definitely identified, because every protein has its specific sequence of the amino acids.

By this identification of the protein one achieves a detailed information on the processes, which are altered in the metabolic pathway and cause the disease. The conclusion is that the reason for the disease can be realized on the molecular level. Where the varied or modified proteins of the disease appear in exceedingly low concentrations, it has not been possible to characterize them clearly until now. Therefore, a more sensitive approach for the determination of the amino acid sequence of the altered proteins is desired which can only be achieved by a drastic miniaturization of the chemical processes in the automate which leads to a detailed protein analysis.

The Edman degradation requests fast changes of different aggressive, delicate and costly sequencer-grade reagents and solvents. It demands temperatures up to 60° C. and the absolute exclusion of oxygen at all parts of the reaction. In order to avoid contamination and the formation of large amounts of by-products, reagent and solvent volumes must be kept as small as possible. This becomes even more essential if only scarce amounts of polypeptides are available, e.g. in the low picomole to femtomole range (corresponding to $10^{-12}$ to $10^{-15}$ mol of sample).

Similarly, the invention can be employed to direct other processes, such as DNA sequencing, amino acid analysis, protein quantification, environmental research and analysis and peptide synthesis within the automate. Characteristic for all these reactions are that they require i.) washes in order to remove salts or other impurities of the biomolecules;

ii.) reactions with organic compounds in order to obtain derivatives suitable for quantitative determination;

iii.) removal of excess reagents and buffers; and iv.) identification and quantification of the derivatives. Typically, aggressive chemicals, organic solvents and higher temperatures are necessary to drive the reactions to completeness. Identification by on-line detection in the appropriate detector system, e.g. UV-, chemical detector or fluorescence detector is mandatory if small sample quantities have to be determined.

Automates designed for DNA sequencing, biochemical or biomedical analysis, and for peptide synthesis also require the delivery of aggressive chemicals and organic solvents which have to be delivered by means of appropriate, non-corrosive dosage valve systems into an appropriate reaction chamber. Hence, also in these automates similar valve- and reactor systems as designed for protein sequencers are provided.

The typical components of all known sequencers are i) dosing valves;

ii) reactors;

iii) convertors/collectors; and iv) detection systems, which in the existing analysis and dosing system are arranged in separate units combined by outer connection lines, e.g., teflon or steel tubings. Some progress in the arrangement of the valves was achieved by the P40 14 602, which describes a dosing system with numerous pneumatically governed valves, whereas the valves are arranged in a circular mode on a carrier of ringform.

Disadvantageous of all the known technical solutions is, that within and in-between the separate units exist long transportation distances. The units are, e.g., connected by PTFE tubes, which are extremely permeable to oxygen. This fact and the large number of connecting devices results in the penetration of oxygen. This affects the process in several places and the identification by the formation of additional derivatives; and the coupling of the reagent to the next amino acid may be directly blocked. Moreover, the yields of the cleaved amino acids are drastically reduced due to partial destruction.

Another important disadvantage, i.e. limiting factor of the existing systems, is that the smallest dosable quantity of chemicals is approximately 5 µl. If a very small quantity of the sample is applied, the protein which is to be analyzed is washed out rapidly. The sequence can no more unequivocally be identified. Therefore, at present, the minimum amount of ca. 20 pmol protein is necessary, to determine the sequence unambiguously.

SUMMARY OF THE INVENTION

The object of the invention is the construction of a reliable, easy-maintenance analysis and dosing system for long term use.

The analysis system designed serves for multi-purpose analysis of biomolecules, e.g., i) sequencing of the amino acids in polypeptides;
ii) quantitative determination of amino acid composition in polypeptides;
iii) sequencing of nucleotides in DNA or RNA;
iv) quantification of polypeptides or polynucleotides or other biomolecules (e.g. carbohydrates). The analysis system also serves applications in environmental analysis and research such as quantitative or qualitative detection of trace elements or toxic molecules in water. The layout of depressions, dosage values, reaction chamber(s) and converter(s)/collector(s) within a wafer based construction serves as units for the derivatization and analysis of these biomolecules within the wafer. By this means, exclusion of oxidants, oxygen and other contaminants of the atmosphere is possible, and the individual parts within the wafer unit connected by short cavities/channels within the wafer construction. Exceedingly small amounts of liquids can be delivered, in e.g. nano-liter amounts to perform reactions on minute samples, in the low femto- to attomole range.

The different components within the wafer-based construction, e.g., the delivery valve system(s), reactor(s), converter/collector, on-line-capillary for the separation detection/quantification, are connected by channels that can be combined in different ways by operating the appropriate valves depending on the chemical reaction performed. The design within the wafer is made in a manner that allows performance of different reactions, degradations, and derivatizations as well as separation processes, mixing, extracting or such leading to a multi-purpose-multifunctional device.

The sample, dissolved for analysis, may be introduced via the delivery valve system, or alternatively, by inserting it applied onto an appropriate solid or membrane support, into the reactor device within the wafer. Accordingly, the device described below can be applied for analysis, sequencing or derivatization or biomolecules, and is not limited to one of these reactions/purposes. When used for the derivatization and quantification or biomolecules, detection by ion-selective methods, UV-absorption, dye or fluorescence detection or chemical detection may be employed.

The invention described enables the exact and reproducible dosage as well as the analysis of the smallest amounts of substances and short connection distances in-between the components. It also guarantees the nearly complete exclusion of contaminants and eliminates penetration of oxygen and oxidants. Over all, the production is easy with low costs.

A further object of the invention is to define a process for the production of analysis and dosage systems, which is based on the latest technologies and materials developed for microelectronics.

A special advantage of the invention is, that using the present analysis and dosing system, the primary structure of proteins can be determined in femtomol to attomole amounts. This is achieved by arranging the essential elements and valves on a chip or wafer, consisting of a one- or multilayered substrate and a one- or multilayered cover. The substrate and/or the cover have depressions/grooves in order to build cavities and/or more depressions for the co-operation of the units.

As the substrates consist of semiconducting material such as silicon, or ceramic material, aluminumoxide or glass that may be equipped or covered with a chemically inert layer, the application of most modern microelectronic technologies within the production process of the analysis and dosing system is possible. Factually it sets up an integrated circuit for the inlets and outlets and the connecting lines for the transport of the chemicals, gases and samples as well as for the reactor, converter and detection system. This is achieved by arranging the essential components, valves and at least partly the related lines on a chip which consists of a one- or multilayer substrate with a cover. Through microelectronic structuring processes, depressions are located in the substrate and/or the cover, which are totally or partially converted, by joining substrate and cover, into cavities. Depressions or grooves which are not covered because of partial covering are closed by additional construction elements.

The influence of oxygen, oxidants or contaminants is minimized by the exclusion of discrete connecting lines and the application of airtight adhesives or suitable connection technologies for the fixing of construction elements.

The operation of the valves, which consists of piezoelectric elements and/or are built by pressurized membranes and/or actuators, is dead-volume free so that all chemicals are completely separated from each other and it is guaranteed that no cross contamination or the formation of salt at the reaction of an acid with a reagent/dye takes place. The smallest dosable amount of liquid is defined by the minimal distance between two valves and the geometry of the channel between the valves.

It is also possible, that the valves are built in a multilayer arrangement or consist of polysilicon elements, respectively, the operating of the valves is done by volume-variable material.

The invention shall be described in more detail with the following application examples in the figures.

DETAILED DESCRIPTION

Figure 1:
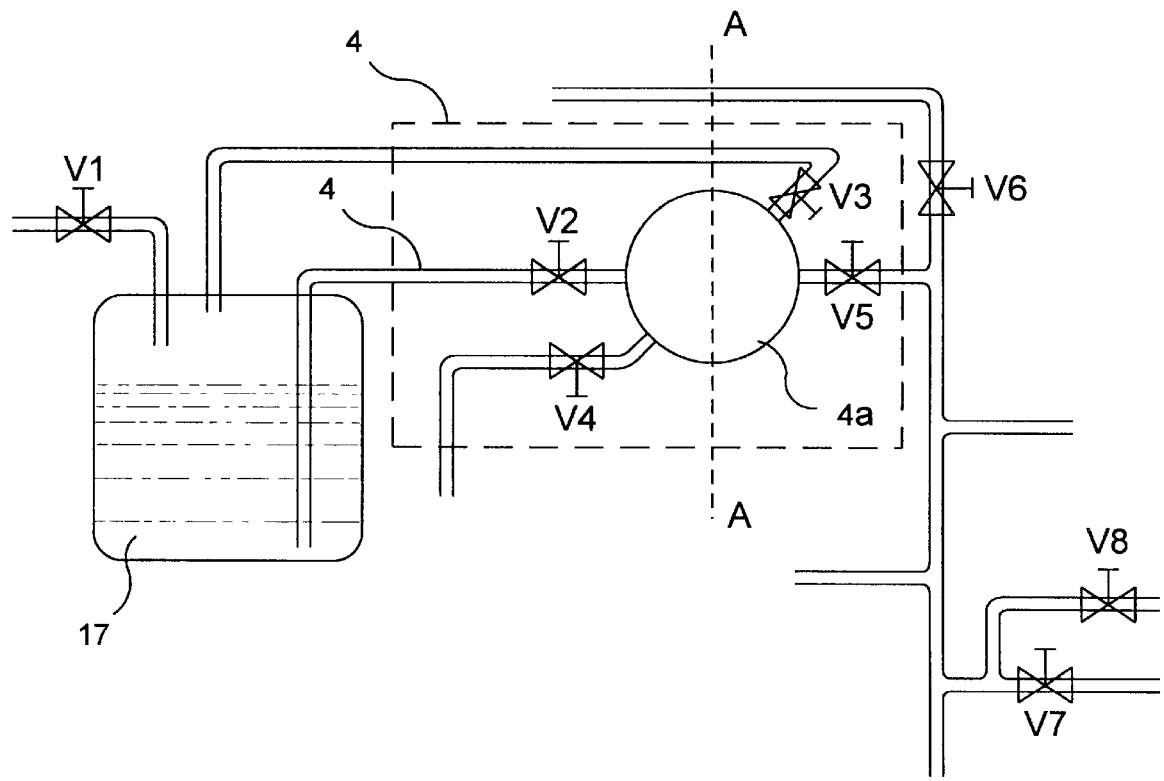
FIG. 1 A schematic plan view of a dosing system arranged on the substrate without cover.
Figure 2:
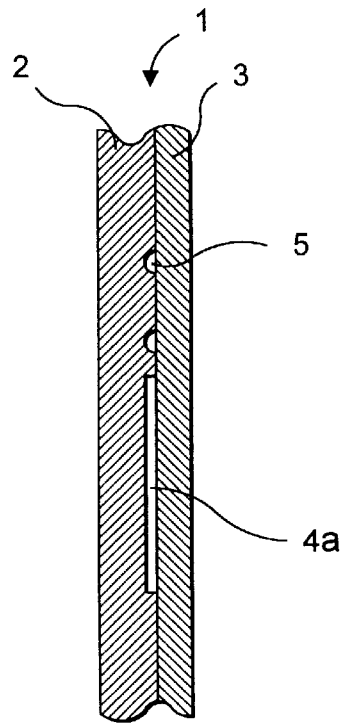
FIG. 2 A cross sectional view of FIG. 1 with a cover, section A—A.

In FIGS. 1 and 2 are shown a section of an analysis and dosing system. On the chip 1 are arranged delivery channels 4 and a depression 4a (here a dosing chamber for the exact volumetric metering of a reagent) for the co-operation with reactor 6a, and valves V2 to V5. In the present example, chip 1 consists of a substrate 2 and a cover 3 made from silicon.

Figure 3:
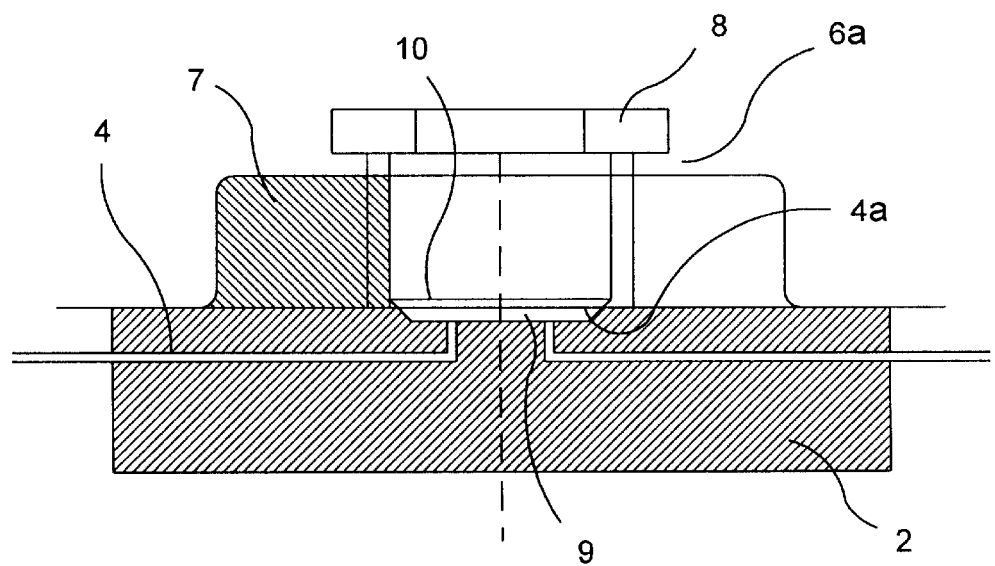
FIG. 3 A reactor chamber arranged on a chip.

Depressions 4 and 4a are structured in the substrate 2 with laser facilities. They are converted into cavities by joining substrate 2 and cover 3. In order to mount the reactor 6a on the substrate, the cover above the depression 4a is interrupted as shown in FIG. 3. The reactor 6a is glued with an airtight (non-permeable) adhesive on the substrate 2. The operation of the valves in the present example is realized by channel interruption and by a cover of a nonpermeable membrane. This membrane can be lifted by pressure variation and thereby the line is opened for flow.

The operation precess per FIG. 1 is:

By opening valve V1, nitrogen pressure is applied on a liquid bottle with a reagent 17 closed tightly to the outside. Subsequently, the valves V2 and V3 are switched into the open position and liquid flows through depression 4, which co-operates with cover 3 to build up cavities 5. By closing the valves V2 and V3 at the same time an exact metered liquid volume is locked within the cavity. Now valves V4 (nitrogen supply), V5 (outlet to the reactor dosing channel) and V7 (inlet to the reaction chamber 6a) are opened. Cleaning of the line is achieved by delivering nitrogen or solvent through the valves V6 and V8. Several of these dosing units allow the delivery of different reagents one after the other to the reaction chamber 6a.

Figure 1A:
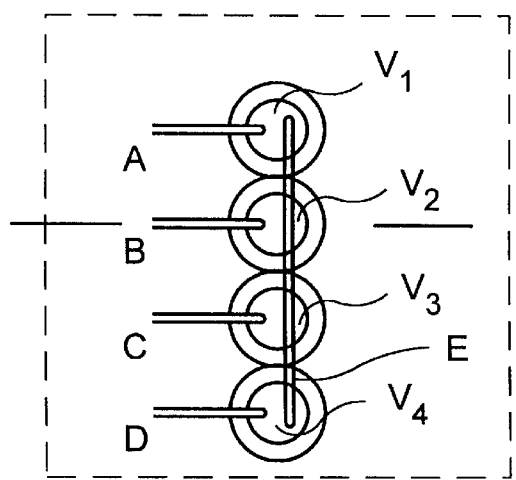
FIG. 1a An alternative arrangement for the function of a dosing channel, shown without cover.

In the arrangement shown in FIG. 1A, the dosing and delivery of chemicals is made as described in the following:

The chemicals to be delivered are transported through line/channel B. By opening valves V2 and V3, the chemicals flow through line E to recoil C. By closing both valves V2 and V3, an exact metered liquid volume is locked in the channel E between both valves, wherein the channel might have several geometric designs, for example semi-circular, as well as different enlargements of the cross-section of the channel can occur. By opening valves V1 and V4, the enclosed amount of liquid can be transported to outlet D by applying an inert gas overpressure. This might be set up as a single dosing unit as it is shown in FIG. 1A for the construction version "channel/membrane valve." It also may occur, that it is assigned for more than one inlet or outlet line. Depending upon the arrangement, different or equal volumes of dosing are achieved for the different liquids applied.

The construction of a reaction chamber 6a is represented in FIG. 3. In the (multi-layered) substrate 2 is laid depression 4a, for taking up solid samples or samples applied to solid supports, as well as inlet and outlet 4. On the substrate 2 is bonded a housing 7 for the lid 8, which might be opened in order to apply solid samples. It is also possible to apply another substrate fixing connection type. The air- or vacuum-tight closure is guaranteed by suitable adaption of faying surface 9 or a sealing 10.

Figure 4:
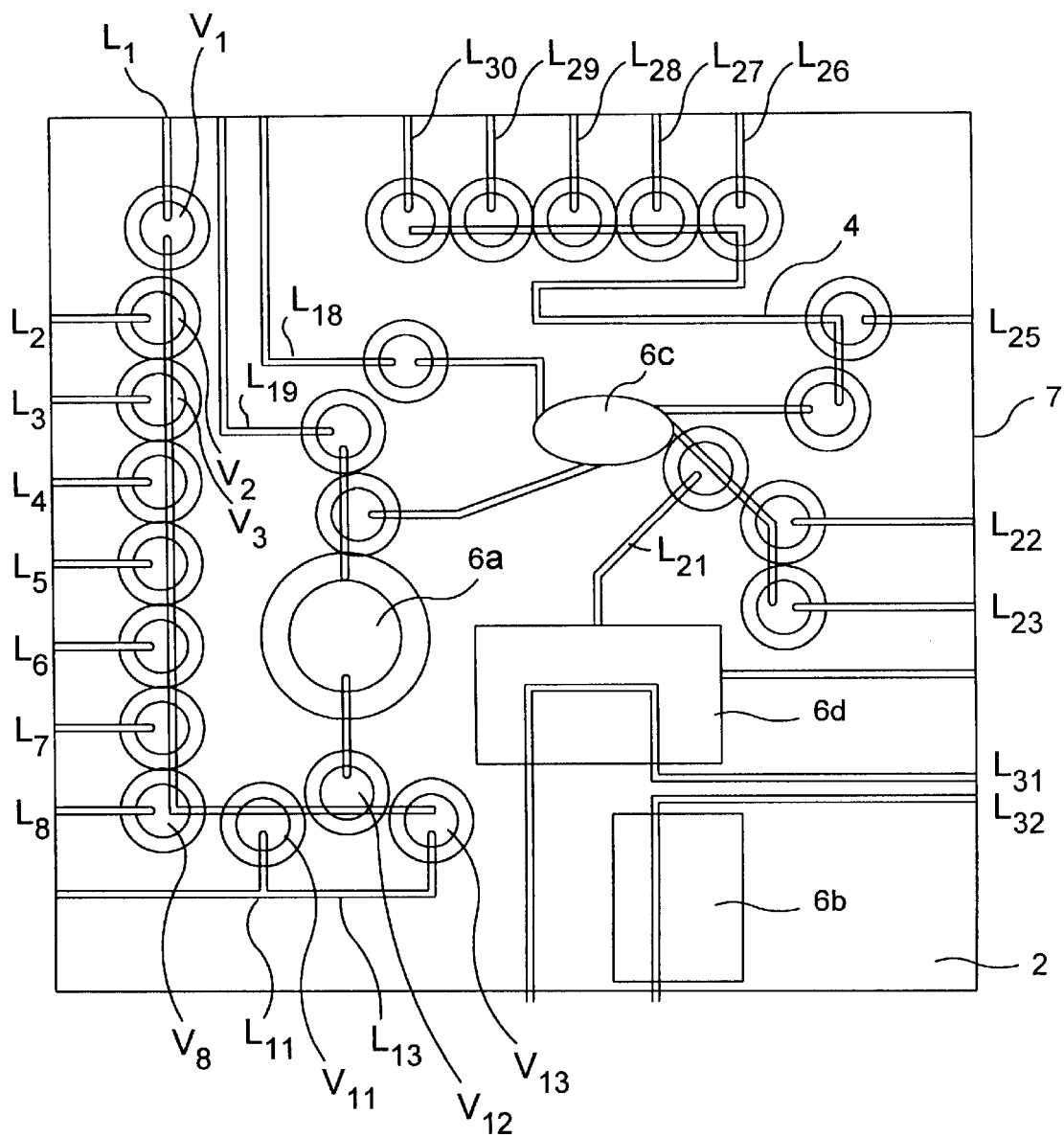
FIG. 4 A complete arrangement of essential constructing elements of a sequencer on a chip/wafer.

FIG. 4 represents a possible arrangement fitted for the function as a protein sequencer unit. On the chip 1 are arranged the valves V1 to Vm as well as the reactor 6a, detector 6b, convertor 6c, and injection valve 6d. The connection between the construction elements results by depressions 4 which are transformed into cavities 5. On chip 1 are arranged different sensors (not shown) which control the transport of the substances, the temperature in reactor 6a and converter 6c as well as further parameters of the process. The measured values are sent to the governing devices, which control actuators or heating elements (not shown in FIG. 4).

A sequence analysis of a protein is done as follows:

The lines L1, L2, L30, and L22 are connected to an inert gas supply. The applied pressure is regulated by throttle valves (not shown). The lines L3 to L8 and L26 to L29 are connected to the solvent and reagents reservoir bottles. The lines L11, L13, L18, L19, L23 and L25 lead to a waste bottle. The sample is applied into reactor chamber 6a, which is closed airtight thereafter. Successively, the chemicals and solvents applied for the Edman degradation are delivered from the bottles (not shown) via lines L3 to L8, and valves V3 to V8, V12 to the reaction chamber 6a under opening of exit valve V19. The amount of chemicals is limited by time control of the dosing valves V3 to V8 or, the dosing technique as described above is applied. This means the cavity in between valves e.g. V8 and V11 is filled with a reagent until the outlet of line L11 is reached. A sensor which is also arranged on chip 1 is set up at the outlet line of valve V11 so that the delivery valves are closed automatically. Afterwards, the liquid is delivered into the reaction chamber 6a by opening the valves V 1 and V12. After the coupling reaction, the cleavage reaction takes place in the reactor and the N-terminal amino acid is cleaved off and extracted by solvents and transferred into the conversion unit. There it is derivatized by further doses of chemicals, e.g. delivered from line L27 via valve 27 to convertor 6c. Then, by applying inert gas and/or heat and/or vacuum, the amino acid derivative is dried and subsequently dissolved in the mobile phase of the detection system. The dosage of chemicals on the conversion side is performed analogous to the dosage of chemicals at the reaction side. While derivatizing one amino acid in the converter, the next N-terminal amino acid is coupled with the reagent and cleaved off the remaining polypeptide chain in the reactor chamber 6a. The derivatized amino acids are transported within line L21 to the injection system 6d—of a HPLC system or a capillary electrophoresis system.

The identification of the sample is done, e.g. by determining the retention time in a micro-bore HPLC column or alternatively, in a capillary HPLC-column or electrophoresis capillary, which is attached to the lines L31 and L32.

For the application of DNA sequencing, a slightly changed setup to FIG. 4 (not shown) is used. Four reaction chambers are arranged on the wafer. Aliquots of the DNA sample are delivered to the reaction chambers and the sample is immobilized on a suitable carrier material. Subsequently, a marker is coupled to the DNA and then the DNA is cleaved with four special reagents parallel in the four reaction chambers. Afterwards, the DNA fragments are transported to the detection system, e.g. four parallel capillary electrophoresis systems.

Another preferred application of the described system for analysis and dosing is environmental analysis and research. Another slightly changed setup to FIG. 4 (not shown) is used for the parallel determination of different solved ions in a sample, e.g. from the waste water treatment. Therefore, aliquots of the sample are delivered to different reaction chambers. Subsequently, reagents, which perform a calorimetric reaction proportional to the concentration are delivered from the reagents reservoir bottles via the lines and valves into the reaction chambers. After the reactions take place, the samples are delivered to a curvette which is arranged on the wafer. The concentration is measured by measuring the optical density of the sample.

Figure 5A:
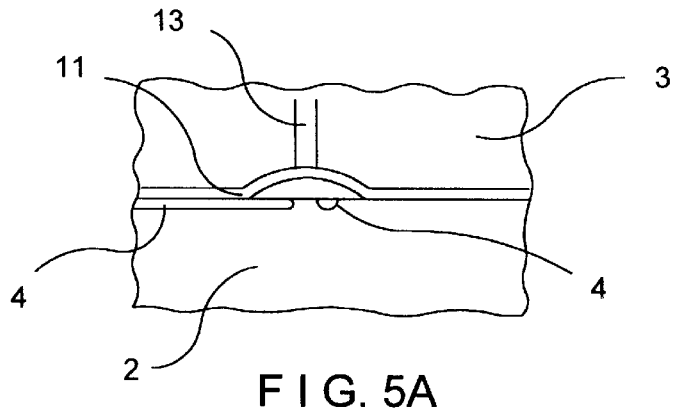
FIG. 5A Shows a detailed construction of a dead-volume free membrane valve in the opened position.
Figure 5B:
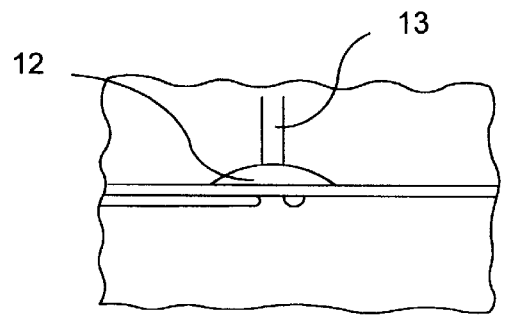
FIG. 5B Shows a detailed construction of a dead-volume free membrane valve in the closed position.

The FIGS. 5A and 5B represent a detailed construction of a dead-volume free membrane valves on the basis of chips. They show the valves in a cross sectional view in the positions opened (FIG. 5A) and closed (FIG. 5B).

The valves operate as follows:

In the substrate 2 are structured depressions (channels) 4.

By use of membrane 11, the depressions are closed air-tight. In the cover 3 at defined positions there are excisions (cut outs). They are connected with a tube 13 to a pneumatic governing valve (not shown). By switching the governing valves, an overpressure or vacuum is applied onto the membrane 11. If an overpressure is applied to membrane 11, the valve is closed dead-volume free (FIG. 5B). In case of sucking up the membrane by vacuum, the liquid can flow from the inlet line through the now existing space into the outlit line. By switching the governing valve again, overpressure is applied to membrane 11 which closes the valve. The reagent's inlet line is closed and the liquid in the delivery line is transported by an inert gas overpressure applied to the line. As a result, the delivery of the liquid out of the cavity into the outlet line takes place.

Figure 6A:
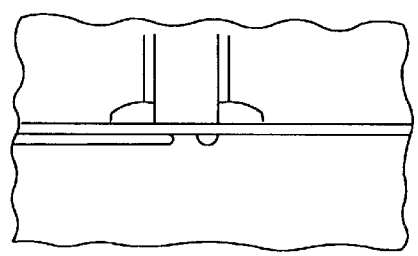
FIG. 6A Shows a cross-sectional view of a membrane valve.

FIG. 6a shows the cross-sectional view of a membrane valve, where the membrane is moved by an actuator, e.g. a piezoelectric element or a magnetic plunger.

Figure 6B:
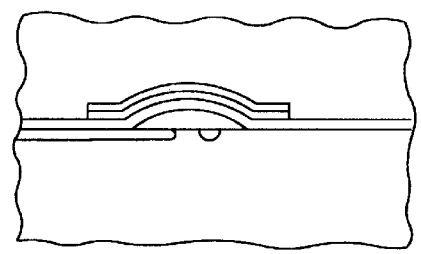
FIG. 6B Shows a cross-sectional view of a further embodiment of a membrane valve.

FIG. 6b represents the cross-sectional view of a membrane valve where the membrane is made by a multilayer arrangement. The movement of the membrane is done by, e.g. governed poly-silicon elements or thermal-extensing elements.

It will be understood that the above descriptions are made by way of illustration, and that the invention may take other forms within the spirit of structures and methods described herein. Variations and modifications will occur to those skilled in the art, and all such variations and modifications are considered to be part of the invention, as defined in the claims.

We claim:

1. A microchemical reaction system, comprising;
   a chip or wafer containing the operative elements of said reaction and analysis system, said chip or wafer comprising a first single or multilayer substrate,
   a cover cooperatively attached to said substrate at an interface, forming a substrate/cover assembly, the cover being constructed from a second single or multilayer substrate,
   at least one reactor element contained within said chip and formed at the interface of said first and second substrates,
   a valve system contained within said chip comprised of a plurality of valves, and
   connector lines contained within said chip and at the interface of said first and second substrates for connecting the reactor element with the multiple valve system,
   wherein the reactor element, valve system and connector lines are formed from depressions or grooves in the substrate and the cover, which form cavities when the substrate and cover are cooperatively joined at said interface.

2. The system according to claim 1, wherein the valves in the valve system, or parts thereof are made from material selected from the group including piezo-electric elements, pressurized membranes, multilayer arrangements, polysilicon elements and volume-variable substances.

3. The use of the microchemical reaction and analysis system according to claim 1 in automatic sequencing devices.

4. The use of the microchemical reaction and analysis system according to claim 1 to determine the structure of proteins and peptides.

5. The use of the microchemical reaction and analysis system according to claim 1 to determine the structure of DNA.

6. The use of the microchemical reaction and analysis system according to claim 1 in peptide-synthesis devices.

7. The system according to claim 1 wherein the valves of the valve system are dead volume free.

8. The system according to claim 1, wherein said substrate and said second substrate are made from semi-conducting material.

9. The system according to claim 8, wherein said semi-conducting material is silicon.

10. The system according to claim 1, wherein said substrate and said second substrate are made from material selected from a group including ceramic, glass and plastic.

11. The system according to claim 10, wherein said ceramic material is aluminum oxide and the plastics are halocarbon plastics (PTFE), PEEK, KEL/F or polyimide.

12. The system according to claim 1, wherein said cover consists of single or multilayer sheets or single or multilayer plates or single or multilayer membranes.

13. The system according to claim 12, wherein said cover is made from material selected from the group including PTFE, KEL/F and polyimide.

14. The system according to claim 12, wherein said cover is made of the same material as the substrate.

15. The system according to claim 1, further comprising at least one operational element selected from the group including reactors, detectors, converters, injection valves, micropumps, sensors, collectors, cuvettes, separation units, columns, delivery channels, internal loops and housings, wherein each of said operational elements are contained within the substrate/cover assembly and are cooperatively connected to themselves and the valve system by means of the connectors.

16. The system according to claim 15, wherein said operational elements are glued with an airtight, non-permeable adhesive on the substrate and/or are polymerized on the substrate.

17. The system according to claim 15, wherein said operational elements are assembled by waferbonding with the substrate.

18. The system according to claim 15, wherein the housing or the connectors are arranged to assemble the operational elements on the substrate.

19. A microchemical reaction and analysis system for sequencing and/or analyzing biomolecules as well as for environmental research comprising;
   operational elements, a valve system comprised of a plurality of dead volume free valves, connectors and connecting lines, said operation elements, valve system, connectors and connecting lines being contained on a chip or wafer,
   micromechanical structures with cavities, formed from grooves or depressions, comprising the operational elements and valve system arranged on a chip or wafer wherein the dead volume free valves, the operational elements and the connecting lines are separated and hermetically sealed from each other, so that reagents, chemicals and samples are hermetically separated and enclosed, and are locked in exact defined dosages.

20. The system according to claim 1, further comprising means for chemical analysis.

* * * * *